(12) United States Patent
Yamaguchi

(10) Patent No.: US 6,806,252 B2
(45) Date of Patent: Oct. 19, 2004

(54) BONE-STRENGTHENING AGENTS, FOOD COMPOSITIONS FOR STRENGTHENING BONE AND FEED COMPOSITIONS FOR STRENGTHENING

(75) Inventor: Masayoshi Yamaguchi, Shizuoka (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/257,694

(22) PCT Filed: Apr. 25, 2001

(86) PCT No.: PCT/JP01/03558
§ 371 (c)(1),
(2), (4) Date: Oct. 15, 2002

(87) PCT Pub. No.: WO01/80874
PCT Pub. Date: Nov. 1, 2001

(65) Prior Publication Data
US 2003/0108619 A1 Jun. 12, 2003

(30) Foreign Application Priority Data
Apr. 26, 2000 (JP) ........................................ 2000-125226

(51) Int. Cl.⁷ ......................... A61K 38/16; A61K 31/35
(52) U.S. Cl. .......................................... 514/7; 514/456
(58) Field of Search ..................................... 514/7, 456

(56) References Cited

FOREIGN PATENT DOCUMENTS

| JP | 10-248525 | | 9/1998 |
| JP | 10248525 | * | 9/1998 |
| WO | WO 00/49885 A1 | | 8/2000 |

OTHER PUBLICATIONS

Gao, Ying Hua et al., "Suppressive Effect of Genistein on Rat Bone Osteoclasts: Apoptosis Is Induced through $Ca^{2+}$ Signaling", Biol. Pharm. Bull., (1999), vol. 22, No. 8, pp. 805 to 809.

Masayoshi Yamaguchi and Ying Hua Gao, "Inhibitory Effect of Genistein on Bone Resorption in Tissue Culture", Biochem. Pharmacol., 55, 71–76, 1998.

M. Yamaguchi and Y. H. Gao, "Anabolic effect of genistein on bone metabolism in the femoral–metaphyseal tissues of elderly rats is inhibited by the anti–estrogen tamoxifen", Res. Exp. Med., 197, 101–107, 1997.

Masayoshi Yamaguchi, Ying Hua Gao and Zhong Jie Ma, "Synergistic effect of genistein and zinc on bone components in the femoral–metaphyseal tissues of female rats", J. Bone Miner. Metab., 18, 77–83, 2000.

Patent Abstracts Of Japan, vol. 2000, No. 01, Jan. 31, 2000 of JP 11 269078A (BIOX:KK), Oct. 5, 1999.

* cited by examiner

Primary Examiner—Theodore J. Criares
(74) Attorney, Agent, or Firm—Frishauf, Holtz, Goodman & Chick, P.C.

(57) ABSTRACT

A novel bone-strengthening agent, a bone-strengthening food composition and a bone-strengthening feed composition which aim at preventing a decrease in bone density in association with the onset or progress of osteoporosis. It is found out that not merely added-up effects but synergistic effects can be achieved by the combined use of CPP, which is known as promoting the absorption of calcium essentially required for the soundness of bone and thus exerting an effect of strengthening bone, with genistein which directly acts on the bone tissue, inhibits bone resorption, and promotes osteogenesis and thus exerts an effect of strengthening bone.

18 Claims, No Drawings

BONE-STRENGTHENING AGENTS, FOOD COMPOSITIONS FOR STRENGTHENING BONE AND FEED COMPOSITIONS FOR STRENGTHENING

CROSS REFERENCE TO RELATED APPLICATION

This application is the national phase application of International application PCT/JP01/03558, filed Apr. 25, 2001.

TECHNICAL FIELD

The present invention relates to a bone-strengthening agent, a bone-strengthening food, and a bone-strengthening feed composition, which are capable of preventing a decrease in bone density accompanying the onset or progress of osteoporosis.

BACKGROUND ART

In Japan with an aging society, the number of senior persons who have fallen in a bedridden state because of fracture due to osteoporosis, etc., is increasing. Therefore, it is an extremely important task to prevent osteoporosis. With this as a backdrop, a number of remedies have been developed while studies on preventing osteoporosis by means of food ingredients contained in meals and health foods have been increasing. Also, it is important for increasing cost efficiency to strengthen the bone of domestic animals and poultry, thereby maintaining the soundness thereof, as in humans. On the other hand, it is said that pets require more calcium than humans do in order to make their skeletal frames stronger. Therefore, pet foods dedicated to strengthening bone have been demanded.

In contemplating strengthening bone, it is a key point to promote efficient absorption of calcium, which is a main component of bone and is necessary for maintaining bone sound.

Casein phosphopeptide (hereinafter, abbreviated as "CPP") prepared from proteins in cows' milk has an action of promoting the absorption of calcium and has been practically used as a raw material for a number of foods and feeds. Further, as the invention by which CPP is added to beverages and foods or feeds in order to exhibit the effects of maintaining the bone density and amount of calcium in the bone, reference maybe made to the invention described in JP 10-248525 A. However, this demonstrated no synergism with soybean isoflavone or genistein, one component thereof.

On the other hand, genistein is one of Leguminosae isoflavones and its action of increasing the bone mineral amount has been recently clarified. It has been clarified that genistein has an effect of inhibiting the function of osteoclasts that cause the lysis of bone mineral 10 times as potent as that of daidzein, which is also an isoflavone contained in soybean, etc. (Biol. Pharm. Bull., 22, 805–809, 1999). Further, it is known that genistein directly inhibits the bone resorption by osteoclasts in a culture system using a metaphysial tissue in the femora of old rats (Biochem. Pharmacol., 55: 71–76, 1998) and causes an increase in the amount of DNA, which serves as an index of an increase in bone mineral content and cell growth by osteoblasts (Res. Exp. Med. 197: 101–107, 1997). Furthermore, in 4-weeks old rats, its synergism with zinc on strengthening the bone has been observed (J. Bone Miner. Metab., 18: 77–83, 2000).

An object of the present invention is to provide a novel bone-strengthening agent, a bone-strengthening food composition and a bone-strengthening feed composition that prevent a decrease in bone density in association with the onset or progress of osteoporosis.

The inventors of the present invention have found out that not merely added-up effects but synergistic effects can also be achieved by the combined use of CPP, which is known as promoting the absorption of calcium essentially required for the soundness of bone and thus exerting an effect of strengthening bone, with genistein that directly acts on the bone tissue, inhibits bone resorption, and promotes osteogenesis, thus exerting an effect of strengthening bone. The present invention has been accomplished based on this finding.

SUMMARY OF THE INVENTION

Roughly divided, the present invention includes three types of aspects. That is, a first aspect relates to bone-strengthening agents; a second aspect relates to food compositions for strengthening bone; and a third aspect relates to feed compositions for strengthening bone.

A first aspect of the present invention relates to a bone-strengthening agent characterized by comprising casein phosphopeptide and genistein as active ingredients.

A second aspect of the present invention relates to a bone-strengthening food composition, characterized by comprising casein phosphopeptide and genistein as active ingredients.

A third aspect of the present invention relates to a bone-strengthening feed composition, characterized by comprising casein phosphopeptide and genistein as active ingredients.

Further, in the first to third aspects as described above, the present invention provides those that further contain a mineral in addition to casein phosphopeptide and genistein as active ingredients.

First, for the first aspect, there is provided the bone-strengthening agent described above, characterized by further comprising a mineral as an active ingredient.

Next, for the second aspect, there is provided the bone-strengthening food composition described above, characterized by further comprising a mineral as an active ingredient.

Further, for the third aspect, there is provided the bone-strengthening feed composition described above characterized by further comprising a mineral as an active ingredient.

Furthermore, in the first to third aspects as described above, the present invention provides those in which the above-mentioned mineral is at least one selected from calcium, magnesium and phosphorus.

First, for the first aspect, there is provided the bone-strengthening agent described above and further comprising a mineral, characterized in that the mineral is at least one selected from calcium, magnesium and phosphorus.

Next, for the second aspect, there is provided the bone-strengthening food composition described above and further comprising a mineral, characterized in that the mineral is at least one selected from calcium, magnesium and phosphorus.

Further, for the third aspect, there is provided the bone-strengthening feed composition described above and further comprising a mineral, characterized in that the mineral is at least one selected from calcium, magnesium and phosphorus.

DETAILED DESCRIPTION OF THE INVENTION

As described above, roughly divided, the present invention includes three types of aspects, i.e., the first to third aspects. That is, what belongs to the first aspect relates to bone-strengthening agents as described above; what belongs to the second aspect relates to food compositions for strengthening bone as described above; and what belongs to the third aspect relates to feed compositions for strengthening bone as described above.

The bone-strengthening agent of the present invention as described above, the food composition for strengthening bone of the present invention as described above, and the bone-strengthening feed composition of the present invention as described above, each contains CPP and genistein.

The CPP used in the present invention is casein hydrolysate, which is a phosphopeptide having an activity of solubilizing calcium.

Sources for supplying genistein are not particularly limited and those derived from Leguminosae plants including soybean may be used.

The bone-strengthening agent of the present invention as described above, the food composition for strengthening bone of the present invention as described above, and the bone-strengthening feed composition of the present invention as described above, each further may contain a mineral as an active ingredient.

In this case, as the mineral, at least one selected from three major elements contained in bone, that is, calcium, magnesium and phosphorus, may be used. However, sodium, potassium or other nutritionally indispensable elements such as iron, zinc, copper, chromium, selenium, manganese, and molybdenum may be used without problems.

In the bone-strengthening agent of the present invention as described above, the food composition for strengthening bone of the present invention as described above. and the bone-strengthening feed composition of the present invention as described above, the ratio of CPP to genistein is 500 to 5,000 times, preferably 500 to 1,000 times by weight ratio; the ratio of CPP to calcium is 0.08 times or more by weight ratio, particularly preferably 0.2 to 2 times by weight ratio; the ratio of CPP to magnesium is 0.01 times or more by weight ratio, particularly preferably 0.05 to 1 times by weight ratio; and the ratio of CPP to phosphorus is 0.04 to 4 times by weight ratio.

According to the present invention, the administration of CPP and genistein can significantly increase the contents of bone components in the femora of rats (bone weight, amount of bone calcium, activity of alkaline phosphatase, and amount of DNA).

The effect of it is exerted in both cortical bone (diaphysis) and trabecular bone (metaphysis) regardless of the bone structure of the femora. The simultaneous administration of CPP and genistein exerts an increasing effect stronger than the effects exerted by single administrations of CPP or genistein, in any one of the amount of calcium, the activity of alkaline phosphatase and the amount of DNA in the metaphysial tissue, and this effect is synergistic. In the diaphysial tissue, the simultaneous administration of CPP and genistein brings about a synergistic effect of increasing alkaline phosphatase activity.

The fact that CPP and genistein together have a synergistic effect on the mechanism of controlling the metabolism of bone, as described above, is an effect that cannot be expected from the results of single administrations of CPP or genistein and has an extremely great significance.

And, the effect can be observed not only in young rats but also old rats.

That is, in particular the activity of alkaline phosphatase activity and the amount of DNA in the metaphysial tissue can be synergistically increased by the simultaneous administration of CPP and genistein, as compared with the single administration of CPP or genistein.

This indicates that CPP and genistein together show the effect of increasing the amounts of bone components in senior persons and exerting a preventive effect against a decrease in bone components in the process of physiological senescence.

Therefore, the bone-strengthening agent of the present invention containing CPP and genistein as active ingredients, is useful in that, when in use, it shows the effect of increasing bone components, it can prevent osteoporosis, which is a serious problem to senior persons, and prevent a decrease in bone density in association with the onset or progress of osteoporosis.

And, by using the food composition for strengthening bone of the present invention, containing CPP and genistein as active ingredients, the effects of increasing bone components and preventing osteoporosis or preventing a decrease in bone density in association with the onset or progress of osteoporosis can be obtained concurrently with taking meals and without troubles of taking drugs.

Further, by using the bone-strengthening feed composition of the present invention containing CPP and genistein as active ingredients, strengthening the bone of domestic animals and poultry can be achieved and soundness thereof can be maintained, so that the cost effectiveness can be improved. Also, strengthening the bone of pets can be achieved and thus soundness thereof can be maintained.

Hereinafter, the present invention will be described in detail by examples. However, the present invention should not be considered as being limited thereto.

EXAMPLE 1

1) The materials and methods in Example 1 were as follows.
[Test Animal]
5-weeks old female Wistar rats (Convention) obtained from Japan SLC, Inc. (Hamamatsu, Japan) were used.
[Test Animal Group (Administered Group)]
1. Control group: Basic feed (solid feed for rats, MF, manufactured by Oriental Yeast Co., Ltd.)
2. CPP-administered group: Basic feed+CPP (40 mg/100 g body weight)
3. Genistein-administered group: Basic feed+genistein (50 $\mu$g/100 g body weight)
4. CPP+genistein-administered group: Basic feed+CPP (40 mg/100 g body weight)+genistein (50 $\mu$g/100 g body weight)

The above-mentioned basic feed contained 57.4% of carbohydrate, 1.15% of calcium, 0.25% of magnesium, and 0.88% of phosphorus.

As the CPP, a solution of CPP-III (casein phosphopeptide content 85%) manufactured by Meiji Seika Kaisha, Ltd., dissolved in distilled water was used. As the genistein, a reagent (manufactured by Sigma Chemical Company in U.S.A.) extracted from soybean and highly purified, dissolved in a 10% ethanol solution was used.
[Feeding and Administration Methods]

Animal groups each consisting of five animals were fed with the basic feed under constant temperature and constant humidity conditions of room temperature 25° C., and 55% humidity. In addition, the control group was administered with 1 ml/100 g body weight of purified distilled water and the other groups were each orally administered with CPP and/or genistein in the above-mentioned amounts once a day for 14 days by using a stomach tube. After 24 hours from the last administration, the rats were sacrificed and the femora were extracted. The extracted femora were used for the measurement of bone components as shown below.

[Measurement of the Dry Weight of a Bone Tissue (Femora) and the Amount of Calcium in the Bone Tissue]

After washing the extracted femora in a cold 0.25 M sucrose solution to remove a soft tissue and drying it in a drier at 100° C. for about 16 hours, the dry weight of the femora was measured. After the measurement, the extracted femora were divided into diaphysis (cortical bone) and metaphysis (trabecular bone) and the amount of calcium in each of them was measured. That is, the obtained diaphysial tissue and metaphysial tissue of the femora were each charged in a test tube, to which was added 3 ml of concentrated nitric acid to decompose them at 120° C. for 24 hours. The solutions were used as sample solutions and the amount of calcium therein was determined by using an atomic absorption spectrophotometer. The amounts of calcium were expressed in terms of mg per 1 g of the dry weight of the bone tissue.

[Measurement of Bone Alkaline Phosphatase Activity]

The diaphysial tissue and metaphysial tissue of the femora obtained as described above were each dipped in 3 ml of a cold 6.5 mM barbital buffer (pH 7.4) and cut into small pieces and homogenized by using a Potter-Elvehjem homogenizer followed by ultrasonic treatment for 60 seconds for crushing. Further, the homogenate was centrifuged for 5 minutes at 600×g and the supernatant fraction was used as a crude enzyme solution.

The activity of bone alkaline phosphatase was measured in accordance with the method of Walter and Schutt (Bergmeyer H. U. (ed.). Methods of Enzymatic Analysis, Vol. 1–2, Academic Press, New York, pp. 856–860, 1974). The enzymatic reaction was initiated by adding 0.05 ml of the above-mentioned crude enzyme solution to 2 ml of 0.1 M diethanolamine hydrochloride buffer (pH 9.8) containing disodium p-nitrophenyiphosphate as a substrate. The reaction was performed by incubation at 37° C. for 30 minutes. The reaction was terminated by adding 10 ml of 0.05N NaOH and the activity was expressed in terms of the amount ($\mu$mol) of free p-nitrophenol per 1 minute per the mass (mg) of the enzyme protein used. The concentration of the protein was measured in accordance with the method of Lowry et al. (J. Biol. Chem., 193: 265–273, 1951).

[Measurement of Deoxyribonucleic Acid (DNA) in Bone Tissue]

The diaphysial tissue and metaphysial tissue of the femora thus obtained were each crushed in 4.0 ml of a cold 0.1 N NaOH solution after homogenization of the bone tissue, shaken at 4° C. for 24 hours and extracted. After the alkali extraction, centrifugation treatment was performed at 1,000×g for 5 minutes and the supernatant fraction was used as a sample for the measurement of DNA. The measurement of the amount of DNA was performed in accordance with the method of Ceriotti (J. Biol. Chem., 214: 39–77, 1955). To a test tube containing 2.0 ml of a sample were added 1.0 ml of concentrated hydrochloric acid and 1.0 ml of a 0.04% indole solution and the test tube was shut with an aluminum cap, followed by heating on a boiling water bath for 10 minutes and then quenched on ice to terminate the reaction. Extraction with 4.0 ml of chloroform for 3 to 4 minutes was repeated several times and the amount of DNA was measured on a spectrophotometer (490 nm). The amount of DNA was calculated per wet weight (g) of bone tissue.

[Statistical Treatment Method]

Significant tests of respective measured values were performed by using Student's t-test. Values with a risk factor of 5% or less were taken as significant.

2) Results

[Body Weight]

The body weight after completion of the feeding was 111.4±2.7 g in the control group, 112.2±0.9 g in the CPP-administered group, 123.8±1.2 g in the genistein-administered group, and 119.0±1.9 g in the (CPP+genistein)-administered group. The genistein-administered group ($p<0.01$) and the (CPP+genistein)-administered group ($p<0.05$) had significantly higher body weights than that of the control group.

[Dry Weight of Femora]

The results of measurements of the dry weight of femora are shown in Table 1. The dry weight of femora, as compared with that of the control group, increased to 1.09 times in the CPP-administered group, 1.12 times in the genistein-administered group, 1.18 times in the (CPP+genistein)-administered group, each showing a significant increase. The increasing action in the (CPP+genistein)-administered group was additive.

TABLE 1

Dry weight of femora

| Administered group | Dry weight of femora (mg) |
| --- | --- |
| Control group | 204.9 ± 2.60 |
| CPP-administered group | 222.5 ± 3.10* |
| Genistein-administered group | 230.4 ± 1.20* |
| (CPP + genistein)-admninistered group | 241.6 ± 1.82*,# |

*$p < 0.01$ (as compared with that of the control group)
$p < 0.01$ (as compared with that of the CPP-administered group or genistein-administered group, that is, as compared with the effects of the cases where CPP or genistein was administered singly)

[Amount of Calcium in Femora]

The amounts of calcium in femora, which serve as indices of the amounts of bone minerals, are shown in Table 2. The amount of calcium in the diaphysis, as compared with that of the control group, increased to 1.09 times in the CPP-administered group, 1.12 times in the genistein-administered group, and 1.21 times in the (CPP+genistein)-administered group, each showing a significant increase. The increasing action in the (CPP+genistein)-administered group was additive. On the other hand, the amount of calcium in the metaphysis, as compared with that of the control group, increased to 1.04 times in the CPP administered group, 1.07 times in the genistein-administered group, and 1.17 times in the (CPP+genistein)-administered group, each showing a significant increase. The increasing action in the (CPP+genistein)-administered group was synergistic.

TABLE 2

Amount of calcium in femora

| | Bone calcium(mg/g dry weight) | |
| --- | --- | --- |
| Administered group | Diaphysis | Metaphysis |
| Control group | 201.6 ± 3.18 | 190.3 ± 4.89 |
| CPP-administered group | 219.2 ± 3.95** | 197.1 ± 3.65 |
| Genistein-administered group | 225.1 ± 3.23** | 204.1 ± 3.56** |
| (CPP + genistein)-administered group | 243.5 ± 2.63**,# | 222.3 ± 4.19**,# |

*$p < 0.05$, **$p < 0.01$ (as compared with that of the control group)
$p < 0.01$ (as compared with that of the CPP-administered group or genistein-administered group, that is, as compared with the effects of the cases where CPP or genistein was administered singly)

[Activity of Femoral Alkaline Phosphatase]

The activity of alkaline phosphatase, which is a marker for the metabolism of bone participating in increasing bone in femora, is shown in Table 3. The activity of femoral alkaline phosphatase in the diaphysis, as compared with that of the control group, increased to 1.02 times in the CPP-administered group, 1.04 times in the genistein-administered group and 1.12 times in the (CPP+genistein)-administered group, each showing a significant increase. The increasing action of alkaline phosphatase in the (CPP+genistein)-administered group was synergistic. On the other hand, the activity of femoral alkaline phosphatase in the metaphysis, as compared with that of the control group, increased to 1.02 times for the CPP-administered group, 1.04 times in the genistein-administered group and 1.18 times in the (CPP+genistein)-administered group, each showing a significant increase. The increasing action in the (CPP+genistein)-administered group was synergistic.

TABLE 3

Activity of femoral alkaline phosphatase

| Administered group | The activity of alkaline phosphatase ($\mu$mol/min/mg protein) | |
|---|---|---|
| | Diaphysis | Metaphysis |
| Control group | 1.737 ± 0.021 | 1.784 ± 0.017 |
| CPP-administered group | 1.779 ± 0.014 | 1.818 ± 0.013 |
| Genistein-administered group | 1.809 ± 0.014* | 1.853 ± 0.017** |
| (CPP + genistein)-administered group | 1.942 ± 0.017**,# | 2.105 ± 0.017**,# |

*$p < 0.05$, **$p < 0.01$ (as compared with that of the control group)
$p < 0.01$ (as compared with that of the CPP-administered group or genistein-administered group, that is, as compared with the effects of the cases where CPP or genistein was administered singly)

[Amount of DNA in Femora]

The amounts of DNA, which serves as an index for the proliferation of cells in femora, are shown in Table 4. The amount of DNA in the diaphysis, as compared with that of the control group, increased to 1.05 times in the CPP-administered group, 1.06 times in the genistein-administered group and 1.12 times in the (CPP+genistein)-administered group, each showing a significant increase. The increasing action in the (CPP+genistein)-administered group was synergistic. On the other hand, the amount of DNA in the metaphysis, as compared with that of the control group, increased to 1.02 times in the CPP-administered group, 1.09 times in the genistein-administered group and 1.23 times in the (CPP+genistein)-administered group, each showing a significant increase. The increasing action in the (CPP+genistein)-administered group was synergistic.

TABLE 4

Amount of DNA in femora

| Administered group | Amount of DNA (mg/g wet weight of bone) | |
|---|---|---|
| | Diaphysis | Metaphysis |
| Control group | 1.788 ± 0.031 | 2.653 ± 0.041 |
| CPP-administered group | 1.886 ± 0.037 | 2.701 ± 0.047 |
| Genistein-administered group | 1.895 ± 0.013* | 2.894 ± 0.034* |
| (CPP + genistein)-administered group | 2.002 ± 0.018*,# | 3.276 ± 0.044*,# |

*$p < 0.05$, **$p < 0.01$ (as compared with that of the control group)
$p < 0.01$ (as compared with that of the CPP-administered group or genistein-administered group, that is, as compared with the effects of the cases where CPP or genistein was administered singly)

EXAMPLE 2

1) The materials and methods in Example 2 were the same as in Example 1 except that 50-weeks old normal female Wistar rats obtained from Japan SLC, Inc. (Hamamatsu, Japan) were used as test animals.

2) Results

[Body Weight]

The body weights of the test animals after completion of the feeding are shown in Table 5. The body weights after completion of the feeding was 228.8±5.9 g in the control group, 227.4±4.4 g in the CPP-administered group, 229.6±7.6 g in the genistein-administered group, and 230.6±7.7 g in the (CPP+genistein)-administered group. The genistein-administered group and the (CPP+genistein)-administered group exceeded the control group, and further, the (CPP+genistein)-administered group exceeded the genistein-administered group. However, none of these groups showed a significant difference to the control group.

TABLE 5

Body weight

| Administered group | Body weight after completion of the feeding (g) |
|---|---|
| Control group | 228.8 ± 5.9 |
| CPP-administered group | 227.4 ± 4.4 |
| Genistein-administered group | 229.6 ± 7.6 |
| (CPP + genistein)-administered group | 230.6 ± 7.7 |

[Dry Weight of Femora]

The results of measurement of the dry weight of femora are shown in Table 6. The dry weight of femora, as compared with that of the control group, increased to 1.06 times in the CPP-administered group, 1.08 times in the genistein-administered group, 1.10 times in the (CPP+genistein)-administered group, each showing a significant increase. The increasing action of the (CPP+genistein)-administered group was additive.

TABLE 6

Dry weight of femora

| Administered group | Dry weight of femora (mg) |
|---|---|
| Control group | 439.3 ± 6.52 |
| CPP-administered group | 464.8 ± 5.68* |
| Genistein-administered group | 475.3 ± 8.35** |
| (CPP + genistein)-administered group | 485.3 ± 8.06**,# |

*$p < 0.025$, **$p < 0.01$ (as compared with that of the control group)
$p < 0.01$ (as compared with that of the CPP-administered group, that is, as compared with the effect of the case where CPP was administered singly)

[The Amount of Calcium in Femora]

The amounts of calcium in femora, which serve as an index of the amounts of bone minerals, are shown in Table 7. The amount of calcium in the diaphysis, as compared with that of the control group, increased to 1.03 times in the CPP-administered group, 1.07 times in the genistein-administered group and 1.09 times in the (CPP+genistein)-administered group, each showing a significant increase. The increasing action in the (CPP+genistein)-administered group was additive. On the other hand, the amount of calcium in femora in the metaphysis, as compared with that of the control group, increased to 1.08 times in the CPP-administered group, 1.08 times in the genistein-administered group and 1.19 times in the (CPP+genistein)-administered group, each showing a significant increase. The increasing action in the (CPP+genistein)-administered group was synergistic.

TABLE 7

The amount of calcium in femora

| Administered group | Amount of bone calcium (mg/g dry weight) | |
| --- | --- | --- |
| | Diaphysis | Metaphysis |
| Control group | 214.6 ± 4.2 | 187.2 ± 4.5 |
| CPP-administered group | 221.8 ± 3.6 | 201.6 ± 3.8* |
| Genistein-administered group | 229.2 ± 3.4** | 202.1 ± 3.8* |
| (CPP + genistein)-administered group | 234.8 ± 3.9*** | 222.4 ± 3.1***,# |

*$p < 0.05$, $p < 0.025$, *$p < 0.01$ (as compared with that of the control)
$p < 0.01$ (as compared with that of the CPP-administered group or genistein-administered group, that is, as compared with the effects of the cases where CPP or genistein was administered singly)

[Activity of Femoral Alkaline Phosphatase]

The activity of alkaline phosphatase, which is a marker for the metabolism of bone participating in increasing bone, is shown in Table 8.

According to Table 8, the activity of femoral alkaline phosphatase in the diaphysis, as compared with that of the control group, increased to 1.06 times in the CPP-administered group, 1.12 times in the genistein-administered group and 1.14 times in the (CPP+genistein)-administered group. Among them, the genistein-administered group and the (CPP+genistein)-administered group each showed a significant increase. The increasing action in the (CPP+genistein)-administered group was additive.

On the other hand, the activity of femoral alkaline phosphatase in the metaphysis, as compared with that of the control group, increased to 1.11 times in the CPP-administered group, 1.12 times in the genistein-administered group and 1.28 times in the (CPP+genistein)-administered group, each showing a significant increase. The increasing action in the (CPP+genistein)-administered group was synergistic.

Furthermore, comparison of Table 8 showing the activity of femoral alkaline phosphatase in 50-weeks old rats with Table 3 showing the activity of femoral alkaline phosphatase in 5-weeks old rats indicates that the activity of femoral alkaline phosphatase is considerably decreased by aging.

TABLE 8

Activity of femoral alkaline phosphatase

| Administered group | The activity of alkaline phosphatase ($\mu$mol/min/mg protein) | |
| --- | --- | --- |
| | Diaphysis | Metaphysis |
| Control group | 0.581 ± 0.017 | 0.669 ± 0.023 |
| CPP-administered group | 0.616 ± 0.021 | 0.742 ± 0.020* |
| Genistein-adiministered group | 0.653 ± 0.019** | 0.744 ± 0.020* |
| (CPP + genistein)-administered group | 0.664 ± 0.021*** | 0.857 ± 0.024***,# |

*$p < 0.05$, $p < 0.025$, *$p < 0.01$ (as compared with that of the control group)
$p < 0.01$ (as compared with that of the CPP-administered group or genistein-adiministered group, that is, as compared with the effects of the cases where CPP or genistein was administered singly)

[Amount of DNA in Femora]

Variations of the amounts of DNA, which serve as an index for the proliferation of cells in femora, are shown in Table 9.

The amount of DNA in the diaphysis, as compared with that of the control group, increased to 1.14 times in the CPP-administered group, 1.14 times in the genistein-administered group and 1.16 times in the (CPP+genistein)-administered group, each showing a significant increase. The increasing action in the (CPP+genistein)-administered group was additive.

On the other hand, the increase in the activity of femoral alkaline phosphatase in the metaphysis, as compared with that of the control group, increased to 1.04 times in the CPP-administered group, 1.05 times in the genistein-administered group and 1.11 times in the (CPP+genistein)-administered group, each showing a significant increase. The increasing action in the (CPP+genistein)-administered group was synergistic.

TABLE 9

Amount of DNA in femora

| Administered group | Amount of DNA (mg/g wet weight of bone) | |
| --- | --- | --- |
| | Diaphysis | Metaphysis |
| Control group | 1.218 ± 0.058 | 2.695 ± 0.047 |
| CPP-administered group | 1.386 ± 0.041* | 2.814 ± 0.039 |
| Genistein-adiministered group | 1.391 ± 0.043** | 2.836 ± 0.041* |
| (CPP + genistein)-administered group | 1.410 ± 0.044** | 3.004 ± 0.042***,# |

*$p < 0.05$, $p < 0.025$, *$p < 0.01$ (as compared with that of the control group)
$p < 0.01$ (as compared with that of the CPP-administered group or genistein-administered group, that is, as compared with the effects of the cases where CPP or genistein was administered singly)

As described above, it was observed that oral administration of CPP (40 mg/100 g body weight) and genistein (50 $\mu$g/100 g body weight) for two weeks caused a significant increase in bone components (bone weight, amount of bone calcium, activity of alkaline phosphatase, amount of DNA) in the femora of rats.

The effect was exerted in both cortical bone (diaphysis) and trabecular bone (metaphysis) regardless of the bone structure of the femora. Simultaneous oral administration of CPP and genistein exerted an increasing effect stronger than the effects by single administration of CPP or genistein in any one of the amount of calcium, activity of alkaline phosphatase and amount of DNA in the metaphysial tissue, and this effect was synergistic. Furthermore, in the diaphysial tissue, the simultaneous administration of CPP and genistein brought about the effect of synergistic enhancement in the activity of alkaline phosphatase.

As described above, it is an effect unexpected from single administration of CPP or genistein that CPP and genistein together have a synergistic effect on the mechanism of controlling the metabolism of bone, which effect has an extremely great significance.

It has revealed that similar effects exist also in the femora of old rats. That is, although the reactivity of the bone tissues in old rats to single administration of CPP or genistein was at low levels, the simultaneous administration of CPP and genistein demonstrated an additive effect of increasing bone components (amount of bone calcium, activity of alkaline phosphatase, amount of DNA) as compared with the single administration thereof. It has been observed that a complex effect is exerted such that in particular, the amount of bone calcium, the activity of alkaline phosphatase, and the amount of DNA in the metaphysial tissue are synergistically enhanced by the simultaneous administration of CPP and genistein as compared with the single administration of CPP or genistein.

This indicates that CPP and genistein also exert an effect of increasing bone components in senior persons, so that they also exert a preventive effect for a decrease in bone components in the process of physiological senescence.

Industrial Applicability

The bone-strengthening agent of the present invention containing CPP and genistein as active ingredients is useful in that, when in use it shows the effect of increasing bone components, it can prevent osteoporosis, which is now a serious problem to in particular senior persons, and can prevent a decrease in bone density in association with the onset or progress of osteoporosis.

And, by using the food composition for strengthening bone of the present invention containing CPP and genistein as active ingredients, the effect of increasing bone components and the effect of preventing osteoporosis and preventing a decrease in bone density in association with the onset or progress of osteoporosis can be obtained simultaneously with taking meals without troubles in association with taking a medicine.

Furthermore, by using the bone-strengthening feed composition of the present invention containing CPP and genistein as active ingredients, strengthening the bone of domestic animals and poultry and maintaining the soundness thereof can be achieved, so that cost effectiveness can be increased. Also, strengthening the bone of pets can be achieved, so that the soundness thereof can be maintained.

What is claimed is:

1. A bone-strengthening agent comprising synergistic effective amounts of casein phosphopeptide and genistein.

2. The bone-strengthening agent according to claim 1, further comprising a mineral.

3. The bone-strengthening agent according to claim 2, wherein the mineral is at least one mineral selected from the group consisting of calcium, magnesium and phosphorus.

4. A bone-strengthening composition comprising (i) a human food and (ii) bone-strengthening agents according to claim 1.

5. The bone-strengthening composition according to claim 4, further comprising a mineral.

6. The bone-strengthening composition according to claim 5, wherein the mineral is at least one mineral selected from the group consisting of calcium, magnesium and phosphorus.

7. A bone-strengthening composition comprising (i) an animal feed and (ii) bone-strengthening agents according to claim 1.

8. The bone-strengthening composition according to claim 7, further comprising a mineral.

9. The bone-strengthening composition according to claim 8, wherein the mineral is at least one mineral selected from the group consisting of calcium, magnesium and phosphorus.

10. The bone-strengthening agents according to claim 1, wherein the casein phosphopeptide is casein hydrolysate which is a phosphopeptide having an activity of solubilizing calcium.

11. The bone-strengthening agents according to claim 10, wherein the genistein is from a Leguminosae plant.

12. The bone-strengthening agents according to claim 11, wherein the Leguminosae plant is soybean.

13. The bone-strengthening agents according to claim 1, which further comprises a mineral which is calcium and wherein the weight ratio of the casein phosphopeptide to the calcium is 0.2 to 2.

14. The bone-strengthening agents according to claim 1, which further comprises a mineral which is magnesium and wherein the weight ratio of the casein phosphopeptide to the magnesium is 0.05 to 1.

15. The bone-strengthening agents according to claim 1, which further comprises a mineral which is phosphorus and wherein the weight ratio of the casein phosphopeptide to the phosphorus is 0.04 to 4.

16. The bone-strengthening agents according to claim 1, further comprising at least one element selected from the group consisting of sodium, potassium, iron, zinc, copper, chromium, selenium, manganese and molybdenum.

17. The bone-strengthening composition according to claim 7, wherein the animal feed is a feed for domestic animals.

18. The bone-strengthening composition according to claim 7, wherein the animal feed is a feed for poultry.

* * * * *